(12) United States Patent
Rogers et al.

(10) Patent No.: US 8,779,387 B2
(45) Date of Patent: Jul. 15, 2014

(54) METHOD AND SYSTEM FOR DETECTING FLUOROCHROMES IN A FLOW CYTOMETER

(75) Inventors: Clare E. Rogers, Plymouth, MI (US);
Jack T. Ball, Ann Arbor, MI (US);
Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 813 days.

(21) Appl. No.: 13/033,299

(22) Filed: Feb. 23, 2011

(65) Prior Publication Data
US 2011/0204259 A1   Aug. 25, 2011

Related U.S. Application Data

(60) Provisional application No. 61/307,089, filed on Feb. 23, 2010.

(51) Int. Cl.
*G01J 1/58* (2006.01)
*G01N 21/64* (2006.01)

(52) U.S. Cl.
USPC .................................... 250/458.1; 250/459.1

(58) Field of Classification Search
CPC ................. G01N 21/6428; G01N 21/6458
USPC .......................... 250/458.1, 459.1
See application file for complete search history.

(56) References Cited

U.S. PATENT DOCUMENTS

| 3,672,402 A | 6/1972 | Bloemer |
| 4,112,735 A | 9/1978 | Mcknight |
| 4,138,879 A | 2/1979 | Liebermann |
| 4,371,786 A | 2/1983 | Kramer |
| 4,448,538 A | 5/1984 | Mantel |

(Continued)

FOREIGN PATENT DOCUMENTS

| EP | 1396736 A | 3/2004 |
| JP | 356169978 | 12/1981 |

(Continued)

OTHER PUBLICATIONS

Rogers et al., The Benefits of Reducing Unnecessary Variability of Flow Cytometers, Accuri Cytometers [online], Dec. 2009 [retrieved on Apr. 12, 2011), http://accuricytometers.com/files/Accuri_Reducing_Variability_Poster.pdf.

(Continued)

*Primary Examiner* — David Porta
*Assistant Examiner* — Mindy Vu
(74) *Attorney, Agent, or Firm* — Jeffrey Schox

(57) ABSTRACT

A method for detecting fluorochromes in a flow cytometer, including: receiving a sample including particles each tagged with at least one of a first fluorochrome and a second fluorochrome, in which the first and second fluorochromes having distinct spillover coefficients; detecting the particles, including detecting the first and second fluorochromes with a first detector and a second detector; forming a data set for detected particles based on the detection of the first and second fluorochromes; characterizing a detected spillover coefficient for each detected fluorochrome from the data set; and sorting the detected particles into predicted fluorochrome populations based on the detected spillover coefficients. A system for detecting fluorochromes in a flow cytometer, including a flow cell, a fixed gain detection system, and a processor that generates a detected spillover coefficient for each detected particle and sorts the detected particle into predicted fluorochrome populations based on the detected spillover coefficient.

27 Claims, 7 Drawing Sheets

(56) References Cited

U.S. PATENT DOCUMENTS

| | | |
|---|---|---|
| 4,559,454 A | 12/1985 | Kramer |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,844,610 A | 7/1989 | North, Jr. |
| 4,933,813 A | 6/1990 | Berger |
| 5,028,127 A | 7/1991 | Spitzberg |
| 5,030,002 A | 7/1991 | North |
| 5,040,890 A | 8/1991 | North, Jr. |
| 5,043,706 A | 8/1991 | Oliver |
| 5,055,556 A * | 10/1991 | Stryer et al. .................. 530/370 |
| 5,083,862 A | 1/1992 | Rusnak |
| 5,139,609 A | 8/1992 | Fields et al. |
| 5,150,313 A | 9/1992 | Van Den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,395,588 A | 3/1995 | North, Jr. et al. |
| 5,403,552 A | 4/1995 | Pardikes |
| 5,469,375 A | 11/1995 | Kosaka |
| 5,539,386 A | 7/1996 | Elliott |
| 5,552,885 A | 9/1996 | Steen |
| 5,684,480 A | 11/1997 | Jansson |
| 5,739,902 A | 4/1998 | Gjelsnes et al. |
| 5,798,222 A | 8/1998 | Goix |
| 5,883,378 A | 3/1999 | Irish et al. |
| 5,920,388 A | 7/1999 | Sandberg et al. |
| 5,981,180 A | 11/1999 | Chandler et al. |
| 6,016,376 A | 1/2000 | Ghaemi et al. |
| 6,039,078 A | 3/2000 | Tamari |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,362,432 B2 | 4/2008 | Roth |
| 7,471,393 B2 | 12/2008 | Trainer |
| 7,486,387 B2 | 2/2009 | Fritz |
| 7,738,099 B2 | 6/2010 | Morrell et al. |
| 7,739,060 B2 | 6/2010 | Goebel et al. |
| 7,843,561 B2 | 11/2010 | Rich |
| 7,996,188 B2 | 8/2011 | Olson et al. |
| 8,004,674 B2 | 8/2011 | Ball et al. |
| 8,077,310 B2 | 12/2011 | Olson et al. |
| 2001/0014477 A1 | 8/2001 | Pelc et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0097392 A1 | 7/2002 | Minneman et al. |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0151741 A1 | 8/2003 | Wolleschensky et al. |
| 2003/0175157 A1 | 9/2003 | Micklash et al. |
| 2003/0202175 A1 | 10/2003 | Van Den et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0219873 A1 | 10/2006 | Martin et al. |
| 2006/0240411 A1 | 10/2006 | Mehrpouyan et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |

(56) References Cited

U.S. PATENT DOCUMENTS

| | | |
|---|---|---|
| 2007/0079653 A1 | 4/2007 | Zuleta et al. |
| 2007/0096039 A1 | 5/2007 | Kapoor et al. |
| 2007/0124089 A1 | 5/2007 | Jochum et al. |
| 2007/0134089 A1 | 6/2007 | Lee et al. |
| 2007/0188737 A1 | 8/2007 | Fritz |
| 2007/0212262 A1 | 9/2007 | Rich |
| 2007/0224684 A1 | 9/2007 | Olson et al. |
| 2008/0055595 A1 | 3/2008 | Olson et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2008/0240539 A1* | 10/2008 | George et al. ............... 382/133 |
| 2008/0263468 A1 | 10/2008 | Cappione et al. |
| 2009/0104075 A1 | 4/2009 | Rich |
| 2009/0202130 A1 | 8/2009 | George et al. |
| 2009/0216478 A1 | 8/2009 | Estevez |
| 2010/0012853 A1 | 1/2010 | Parks et al. |
| 2010/0032584 A1 | 2/2010 | Dayong et al. |
| 2010/0118298 A1 | 5/2010 | Bair et al. |
| 2010/0120059 A1* | 5/2010 | Yan et al. ................... 435/7.1 |
| 2010/0271620 A1 | 10/2010 | Goebel et al. |
| 2010/0302536 A1 | 12/2010 | Ball et al. |
| 2011/0008816 A1 | 1/2011 | Ball et al. |
| 2012/0004859 A1 | 1/2012 | Olson et al. |

FOREIGN PATENT DOCUMENTS

| | | |
|---|---|---|
| JP | 04086546 H | 3/1992 |
| JP | 10227737 A | 8/1998 |
| WO | 2005017499 A | 2/2005 |
| WO | 2005068971 A | 7/2005 |
| WO | 2005073694 A | 8/2005 |
| WO | 2005091893 A | 10/2005 |
| WO | 2006055722 A | 5/2006 |
| WO | 2007100723 A | 9/2007 |
| WO | 2007103969 A | 9/2007 |
| WO | 2008058217 A | 5/2008 |
| WO | 2010101623 A | 9/2010 |
| WO | 2011106402 A | 9/2011 |
| WO | 2011159708 A | 12/2011 |
| WO | 2012030740 A | 3/2012 |

OTHER PUBLICATIONS

Trotter, Compensation: An Instrumental Perspective, BD Biosciences [online], Sep. 10, 2003 [retrieved on Apr. 12, 2011], http://flowcytometry.uchc.edu/resources/pdfs/trotter_instrument_comp.pdf.

* cited by examiner

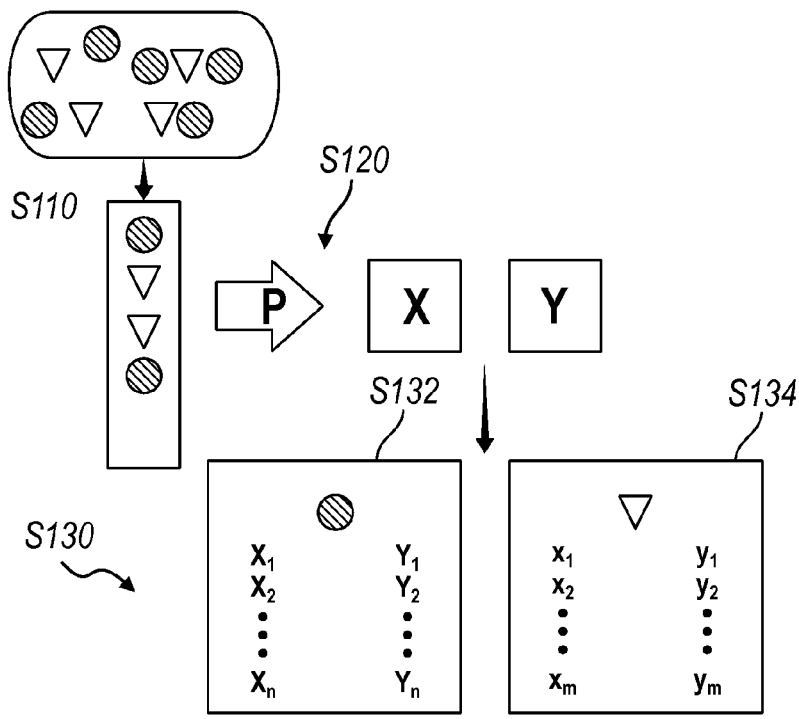
FIG. 2A
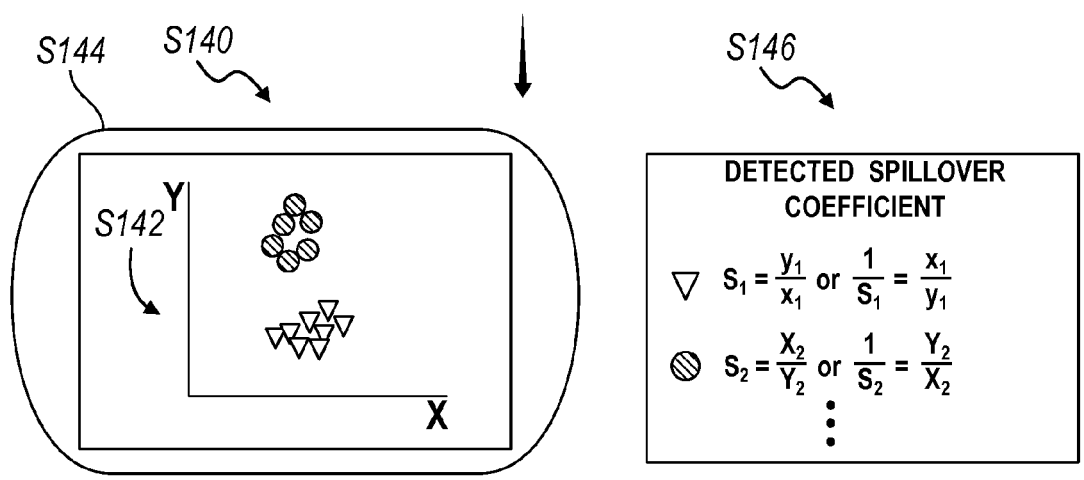
FIG. 2B
FIG. 2C

METHOD AND SYSTEM FOR DETECTING FLUOROCHROMES IN A FLOW CYTOMETER

CROSS-REFERENCE TO RELATED APPLICATIONS

This application claims the benefit of U.S. Provisional Application No. 61/307,089, filed on 23 Feb. 2010, which is incorporated in its entirety by this reference.

TECHNICAL FIELD

This invention relates generally to the flow cytometry analysis field, and more specifically to an improved method and system for detecting fluorochromes in a flow cytometer in the flow cytometry analysis field.

BACKGROUND

Flow cytometers are powerful analytical tools that allow the multi-parametric analysis of up to thousands of particles (such as cells on a cell-by-cell basis) per second. In a flow cytometer, the particles, tagged with fluorescence markers, flow past laser beams in single file. Typically, the parameters that are analyzed include light scatter and fluorescence signals, generated by interaction of the particles with light sources in the flow cytometer. Fluorescence markers, or fluorochromes, may be inherent to the particle or may be added by a user (e.g., researchers or clinicians) to tag specific cellular structures in the sample such as nucleic acids or proteins, or to follow specific cellular processes such as cross-membrane calcium or pH fluxes.

The demand for multi-color and multi-parameter analysis, along with recent advances in optics, electronics, and signal processing, has driven the development of multi-laser, multi-detector systems that can measure up to 30 or more fluorescence signals simultaneously. To satisfy this demand, the typical approach of flow cytometer manufacturers has been to add lasers and detectors to the optical bench of the instrument in proportion to the number of parameters to be measured. This approach assumes that each additional parameter measured will be labeled with a particular fluorochrome requiring a unique detector for analysis. However, this approach greatly increases the size and complexity of the flow cytometer. Further, the price and difficulty of setting up, operating, and maintaining such a flow cytometer quickly moves the system out of reach for most cytometry users who are interested in performing their own analyses. Thus, there is a need in the flow cytometry analysis field to create an improved method and system for detecting fluorochromes in a flow cytometer. This invention provides such improved an improved method.

BRIEF DESCRIPTION OF THE FIGURES

FIGS. 2 and 3 are schematics of various steps of the method of a preferred embodiment;

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
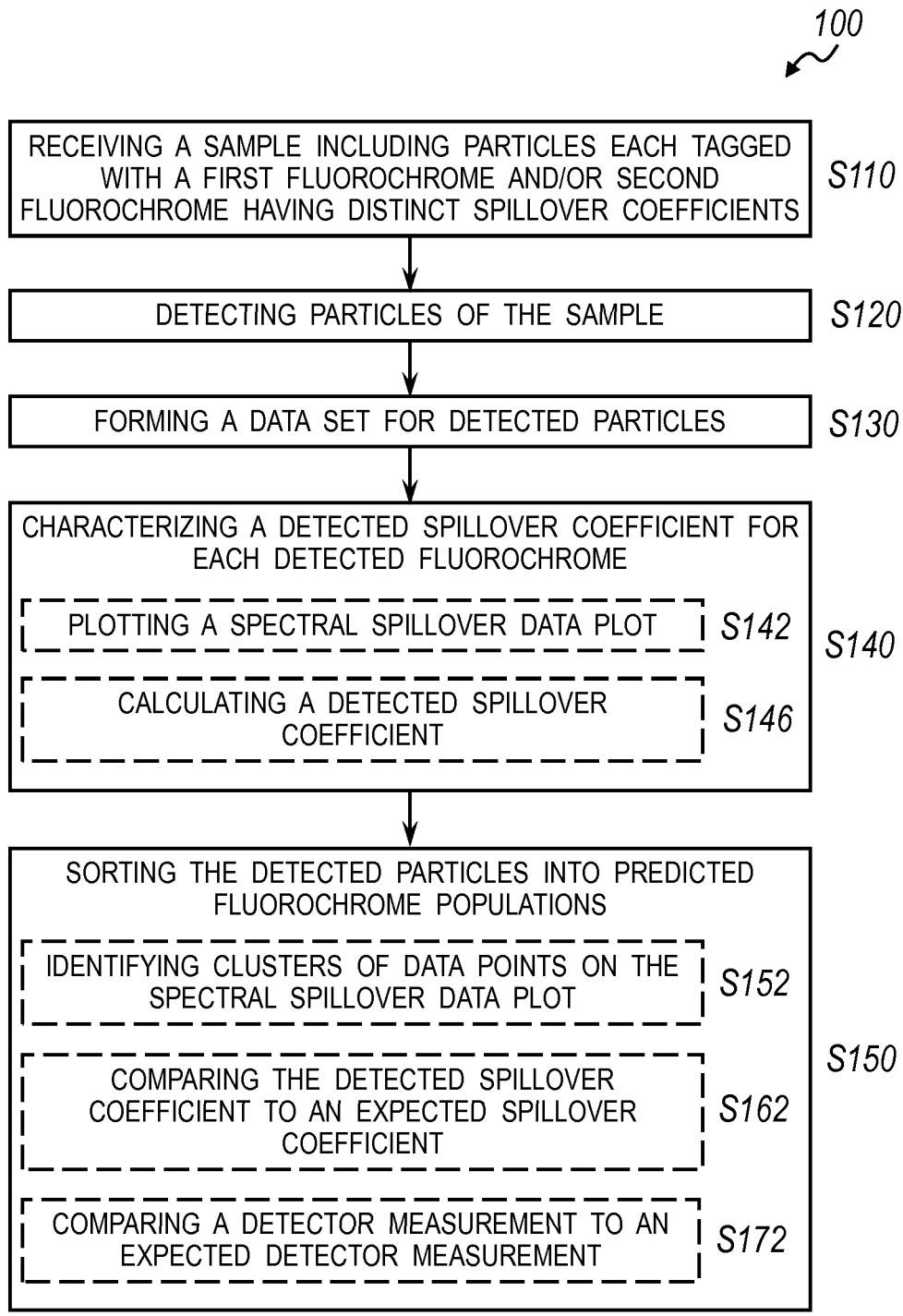
FIG. 1 is a flowchart of various steps of the method of a preferred embodiment.

As shown in FIG. 1, the method 100 for detecting fluorochromes in a flow cytometer of a preferred embodiment includes the steps of: receiving a sample S110 including particles each tagged with at least one of a first fluorochrome and a second fluorochrome, in which the first and second fluorochromes have distinct spillover coefficients; detecting particles of the sample S120, including detecting the first and second fluorochromes of the particles with a first detector and a second detector; forming a data set for detected particles S130 based on the detection of the first and second fluorochromes of the particles; characterizing a detected spillover coefficient S140 for each detected fluorochrome from the data set; and sorting the detected particles S150 into predicted fluorochrome populations based on the detected spillover coefficients. Although spectral spillover is typically considered a nuisance in conventional flow cytometric analysis, the method takes advantage of spectral spillover by utilizing spectral spillover to detect multiple fluorochromes per detector in a flow cytometer, thereby detecting multiple types of particles per detector. For example, the method 100 may further include detecting a third fluorochrome having a third spillover coefficient, without requiring a third detector. The method 100 may be used to analyze samples having particles tagged with any suitable number of fluorochromes having distinct spillover coefficients, including with particles each tagged with a combination of multiple fluorochromes. The particular configuration of fluorochromes and particles will depend on the particular application of the flow cytometry analysis, such as specific clinical or research applications. The method is primarily described here in context of a simpler example of detecting and sorting two fluorochromes with two detectors, but it will be understood by one skilled in the art that the method is preferably expandable to detecting three or more fluorochromes with two detectors, or generally speaking with fewer detectors than the number of distinct fluorochromes.

The step of receiving a sample S110 functions to obtain a sample of particles to analyze with the flow cytometer. The sample (for example, blood) may contain cells and/or any suitable particles or other features of interest that a user would like to track, such as nucleic acids or proteins. As shown in FIG. 2A, each particle is preferably tagged or labeled with one or more particular fluorochromes, and may be inherently tagged with a fluorochrome (such as chlorophyll or phycocyanins in algae) or tagged by a user (such as by binding fluorochromes to antibodies on the particles, or any suitable method). In particular, at least some of the particles in the sample are preferably tagged with a first fluorochrome having a first spillover coefficient and/or a second fluorochrome having a second spillover coefficient, where the first and second spillover coefficients are distinct. In a flow cytometer, fluorochromes are excited and caused to emit detectable light of a spectrum corresponding to the particular fluorochrome. The emission spectra of many fluorochromes are broad enough that the signal for the fluorochrome will typically be picked up or detected by multiple fluorescence detectors in a flow cytometer, resulting in spectral overlap, or "spectral spillover". Furthermore, any single fluorescence detector, while typically having a predetermined and known bandwidth for detecting light, will typically detect multiple fluorochromes. A primary detector (or detector set including one or more optical filters) for a particular fluorochrome is defined as the detector that receives the brightest filtered signal from the fluorochrome (i.e., the most photons), which results in the highest assigned channel number, such as when plotted on a scale of relative intensity for the primary detector. A secondary detector is defined as including any other detector besides the primary detector that also receives a signal from the fluorochrome above background noise, but the signal received by the secondary detector is typically less bright than that received by the primary detector and results in a lowest assigned channel number. Each of the fluorochromes may have identical primary and/or secondary detectors, or may have different primary and/or secondary detectors. The extent of the spectral spillover is measured by a spillover coefficient for a fluorochrome, preferably defined as the median channel number for the fluorochrome in the secondary detector divided by the median channel number for the fluorochrome in the primary detector. For example, a fluorochrome that has a high spillover coefficient provides a brighter signal received by a secondary detector relative to that received by the primary detector, compared to a fluorochrome that has a low spillover coefficient. The first and second fluorochromes may each be one of the following: fluorescein isothiocyanate (FITC), enhanced green fluorescent protein (eGFP), phycoerythrin (PE), phycoerythrin-Texas Red (PE-TxRed), PE-Cy5, PE-Cy7, 7-amino-actinomycin D (7-AAD), allophycocyanin (APC), quantum dot emitting at 525 nm, and quantum dot emitting at 565 nm, which are unique and distinct spillover coefficients. However, the fluorochromes may be any suitable fluorochrome.

The step of detecting the particles of the sample S120 functions to generate data for the flow cytometry sample. In particular, as shown in FIG. 2A, detecting the particles S120 preferably includes detecting the first and second fluorochromes (and potentially any additional fluorochromes) with a first detector X and a second detector Y in the flow cytometer. Detecting the fluorochromes S120 preferably involves exciting the fluorochrome with laser light or any suitable light, filtering fluoresced light emitted by the fluorochrome and scattered by the particles, and detecting the scattered and fluoresced light (photons P) with detectors. Each fluorescence detector is preferably paired with at least one optical filter that filters light emitted by energized fluorochromes, thereby selectively allowing passage of light within a defined range of wavelengths to the detector. Pairing each fluorescence detector with at least one optical filter forms a detector set, such that each detector set is limited to detect light within a particular bandwidth. A detector set may additionally and/or alternatively be limited to detect light within a particular bandwidth by other methods (e.g., the specific design of the detector). In the detecting step S120, each detector is preferably a primary detector for at least one of the fluorochromes and a secondary detector for at least another one of the fluorochromes. For example, the first detector may be the primary detector for the first fluorochrome and the secondary detector for the second fluorochrome, while the second detector may be the primary detector for the second fluorochrome and the secondary detector for the first fluorochrome.

The step of detecting particles S120 preferably further includes detecting the fluorochromes with detectors having a fixed gain, and detecting the fluorochromes with detectors having a broad dynamic range. For instance, detecting the particles S120 is preferably performed by a flow cytometer similar to that described in U.S. Pat. No. 7,739,060 entitled "Detection system and user interface for a flow cytometer system", which is incorporated in its entirety by this reference, although any flow cytometer system with fixed gain and/or a broad dynamic range, or any suitable flow cytometer system, may be used. The detector voltage settings are preferably fixed to a known state and/or in a fixed arrangement, which helps to maintain predictable and consistent fluorochrome spillover coefficients between different sample runs on a single flow cytometer, thereby facilitating reproducible analysis of certain fluorochromes. Since a fixed gain detection system enables reproducible results, fluorescence data collected on some fluorochromes may be mathematically modeled. Furthermore, if multiple flow cytometers have substantially identical fixed detector voltage settings, then the flow cytometers have instrument-to-instrument consistency in fluorescence measurement resulting in consistent spectral spillover configurations, therefore making it easier to compare analysis of sample runs performed among the different flow cytometers. The detector voltage settings may be adjusted or calibrated using a well-defined standard reference, such as Spherotech 8 peak and 6 peak reference beads, such as during manufacture, after servicing of the flow cytometer, periodically, or at any suitable time, to help ensure predictable performance of the detectors and predictable spillover coefficients.

The detectors preferably also have a broad dynamic range, more preferably a range of at least six decades, or at least 16.7 million channels. This broad range enables the flow cytometer to capture a wide range of fluorescence intensities, ensuring high quality data in a variety of applications and fluorescence intensities, without requiring the user to determine and set a proper detection range for a particular experiment. In contrast, other conventional flow cytometers typically have between 1024 and 256,000 channels, which are inadequate to resolve the differences between similar dyes (e.g., FITC and eGFP). In combination, the detectors with fixed gain and a broad dynamic range ensure not only consistent spillover coefficients and less overall variability due to instrumentation and differences in operator input, but also contribute towards a more user-friendly flow cytometer.

The step of forming a data set for detected particles S130 functions to organize the fluorescence data detected by the detectors. The data set is preferably collected in a 24-bit digital signal process across the broad dynamic range of the detectors, but may be collected in any suitable manner. As shown in FIG. 2A, forming a data set S130 includes forming a first data set S132 based on the detection of the first fluorochrome and forming a second data set S134 based on the detection on the second fluorochrome. The first data set preferably includes a pair of channel numbers or each particle detected by the first and second detectors, each channel number corresponding to the brightness of the fluorochrome signal of the particle as detected by one of the two detectors. However, the first data set may include any suitable measure of the first fluorochrome and/or detected particle. The first data set may include an array, such as an array of the channel numbers; for example, an nth detected particle tagged with the first fluorochrome may be represented by a pair of channel numbers in the nth index of an array of the first data set, where the pair of channel numbers includes a primary channel number for the primary detector and a secondary channel number for the secondary detector. The second data set is preferably similar to the first data set, except that the second data set includes data for the second fluorochrome (for particles tagged with the second fluorochrome).

The method may further include any of the following steps: storing the data set (such as on a hard drive or flash memory), printing the data set, and/or exporting the data set to any suitable medium (such as sending the data set through an email or uploading the data set to a server), or any suitable manipulation of the data set.

The step of characterizing a detected spillover coefficient S140 functions to generate an identifier corresponding to each detected particle. In a first variation, as shown in FIG. 2B, characterizing a detected spillover coefficient S140 includes plotting the data set on a spectral spillover data plot S142. The plot may include a portion or the entirety of the first and/or second data sets, with measurements of the first detector on a first axis of the data plot and measurements of the second detector on a second axis of the data plot. In other words, each pair of channel numbers in the first and second data sets preferably corresponds to x- and y-coordinates of a point representing a detected particle. For example, the spectral spillover data plot may include plotted data points representing all detected particles in the flow cytometer sample, such that the horizontal coordinate of a data point is the channel number for the primary detector when detecting a particular particle, and the vertical coordinate of the data point is the channel number for the secondary detector when detecting spectral spillover of the same particle. Plotting measurements of the primary detector against those of the secondary detector is the equivalent of plotting the ratio between the measurements of the two detectors for each of the detected particles, which is by definition the spillover coefficient (or the inverse of the spillover coefficient, depending on which axis of the plot the measurements of each detector is on). The spectral spillover data plot preferably is plotted on a log-log scale, but may alternatively be plotted on a linear scale, a log-linear scale, or any suitable type of scale. In further embodiments, the spectral spillover data plot may include more than two axes. For example, the spectral spillover data plot may include a first axis for detections of a primary detector, and second and third axes for detections of two secondary detectors, to form a 3D plot of the data set or data sets of detected particles.

The method may further include the step of displaying the spectral spillover data plot to a user S144, as shown in FIG. 2B. The spectral spillover data plot may be displayed on a high-resolution user interface, such as a computer screen, but the spectral spillover data plot may additionally and/or alternatively be displayed on any suitable display. Displaying the data plot to the user may allow, for example, the user to visually monitor or review the data sets, or to selectively zoom in on or crop a particular portion of the plot. The method may also further include saving (such as to a hard drive or a server), exporting (such as into another format), and/or printing the spectral spillover data plot, or any suitable manipulations of the plot.

In a second variation, characterizing a detected spillover coefficient S140 includes calculating the detected spillover coefficient S for a detected particle S146 based on the first and second data sets. As shown in FIG. 2C, the detected spillover coefficient for a detected particle is preferably calculated by dividing a data set element corresponding to detection of the particle by a secondary detector by a data set element corresponding to detection of the same particle by a primary detector. In other words, for an ith detected particle in the first data set, the detected spillover coefficient may be calculated by calculating the ratio of the measurements from the primary and secondary detectors for the ith pair of elements in the first data set (such as the pair of channel number elements in the nth index of the first data set). Similarly, for an ith detected particle in the second data set, the detected spillover coefficient S may be calculated by calculating the ratio of the measurements from the primary and secondary detectors for the ith pair of elements in the second data set (such as the pair of channel number elements in the nth index of the second data set). The calculated ratio is preferably the measurement of the secondary detector divided by that of the primary detector to directly calculate the detected spillover coefficient S, but may alternatively be the measurement of the primary detector divided by that of the secondary detector to calculate the inverse of the detected spillover coefficient 1/S (which is also representative of the detected spillover coefficient S). Alternatively, the step of characterizing a detected spillover coefficient S140 may include any suitable calculation or other step.

Figure 3A:
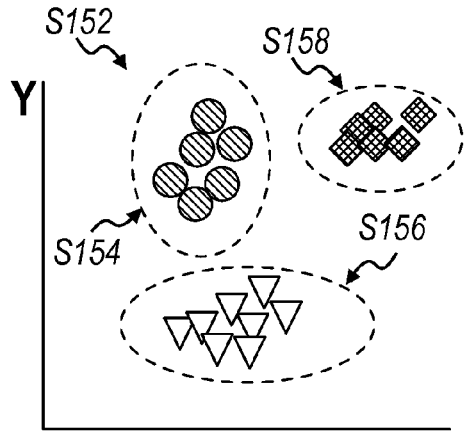

The step of sorting the detected particles S150 into predicted fluorochrome populations based on the detected spillover coefficients S functions to identify particles based on spillover coefficients. In a first variation, sorting the detected particles S150 includes visually identifying clusters of data points on the spectral spillover data plot S152 corresponding to respective fluorochromes. In particular, as shown in FIG. 3A, in this variation sorting the detected particles S150 includes visually identifying a first cluster of data points on the spectral spillover data plot corresponding to the first fluorochrome S154 and identifying a second cluster of data points on the spectral spillover data plot corresponding to the second fluorochrome S156. More complex examples of this variation include identifying a third cluster of data points on the spectral spillover data plot corresponding to the third fluorochrome S158, and similarly for fourth or more populations. Since the data points spectral spillover data plot individually marks a detected spillover coefficient S for a detected particle, detected particles having similar spillover coefficients are typically clustered in the same general location, thereby forming a predicted fluorochrome population. In contrast, detected particles having distinct spillover coefficients are typically clustered in different general locations, thereby forming distinct predicted fluorochrome populations.

Figure 3B:
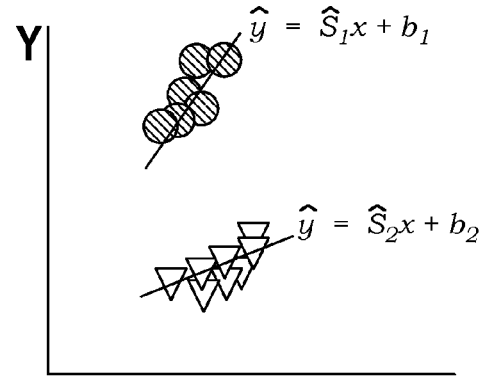

In a second variation, sorting the detected particles S150 includes comparing the detected spillover coefficient to an expected spillover coefficient S162 for a predicted fluorochrome population. The expected spillover coefficient $\hat{S}$ may be at least partially based on previous spectral spillover data plots, or spectral spillover calibration plots. Actual measured data varies slightly among particles tagged with the same fluorochrome such that on a spectral spillover data plot, as shown in FIG. 3B, each predicted fluorochrome population is somewhat distributed and may be characterized by a best-fit line whose slope is associated with the spillover coefficient for that population. The best-fit line and/or slope may be calculated from linear data or log-converted data. The expected spillover coefficient $\hat{S}$ is preferably equal to the slope of the best-fit line obtained from previous spectral spillover calibration plots, which may be constructed similarly to a spectral spillover data plot except with previous data. The expected spillover coefficients from the spectral spillover calibration plots may be used to analyze future samples because the expected spillover coefficients are consistent between different sample analyses, assuming that the method is performed using the same flow cytometer instrument with fixed gain detector settings, or using different flow cytometer instruments having substantially similar fixed gain detector settings. In this variation, the detected spillover coefficients may be defined as a "virtual fluoro channel" whose detection events correspond to the detected spillover coefficients for the detected particles. In this variation, sorting the detected particles S150 includes sorting a detected particle into a first predicted fluorochrome population if the detected spillover coefficient S "matches" the expected spillover coefficient Ŝ of the first predicted fluorochrome population, and similarly sorting a detected particle into a second predicted fluorochrome population if the detected spillover coefficient S "matches" the expected spillover coefficient Ŝ of the second spillover coefficient. A detected spillover coefficient and an expected spillover coefficient may be considered to "match" if their values are within a threshold of each other (such as if the detected spillover coefficient is between a lower and/or upper threshold surrounding the expected spillover coefficient).

In some embodiments, some particles in the sample may be tagged with a single fluorochrome in different concentrations, such that the particles may appear on the spectral spillover plot in separate populations (e.g., one population corresponding to "weakly positive" particles tagged with a lower concentration of the fluorochrome and another population corresponding to "strongly positive" particles tagged with a higher concentration of the fluorochrome). In these embodiments, since the populations correspond to the same fluorochrome, the separate populations may be characterized by separate best-fit lines that have substantially similar slopes and expected spillover coefficients.

Figure 3C:
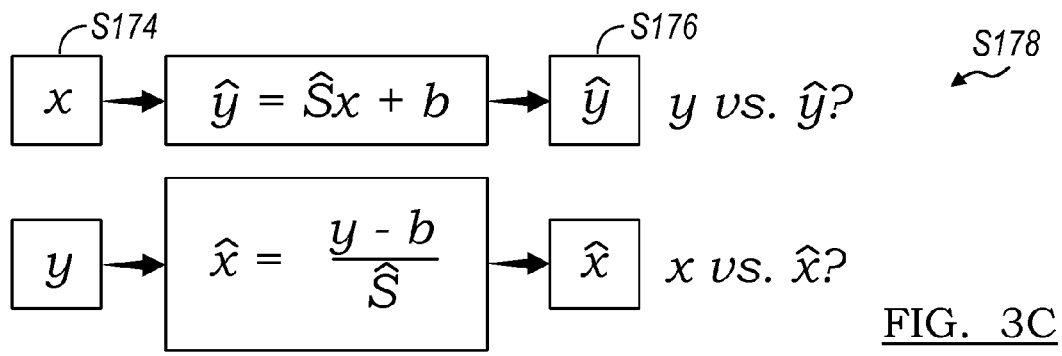

In a third variation, as shown in FIG. 3C, sorting the detected particles S150 includes comparing a detector measurement from the data set to an expected detector measurement S172 estimated with a best-fit line equation of a spectral spillover calibration plot. In this variation, sorting the detected particles S150 preferably includes providing the measurement of one of the first and second detectors as an input S174 into the best-fit line equation from a spectral spillover calibration plot, receiving an output of the best-fit line equation S176 corresponding to an expected measurement of the other of the first and second detectors, and comparing the expected measurement to the actual other measurement S178 of the first and second detectors. In this variation, the best-fit line equation is used to generate an expected secondary detector measurement for a particular detected particle based on a primary detector measurement for the same particle, or alternatively to generate an expected primary detector measurement for a particular detected particle based on a secondary detector measurement for the same particle. The best-fit line equation is preferably similar to that described in the second variation of sorting the detected particles. The expected detector measurement is indirectly based on an expected spillover coefficient as expected by the best-fit line that is based on a spectral spillover calibration plot, such that comparing an expected detector measurement with an actual detector measurement is indirectly comparing the detected and expected spillover coefficient. This variation of the sorting step S150 may be better suited for certain fluorochromes compared to others. Each best-fit line equation has a coefficient of determination or squared correlation coefficient ($r^2$) that provides a measure of how well the best-fit line equation can be used to predict the measurement of one of the detectors based on the measurement of the other detector. For instance, a high $r^2$ value indicates that the best-fit line equation can be used to predict the expected channel number of the secondary detector (y-value) of a detected particle based on the channel number of the primary detector (x-value) for the same detected particle. Conversely, a low $r^2$ value, which typically indicates that there is little spillover into the secondary detector, indicates that the best-fit line equation may be not as well suited for this variation of sorting the detected particles S150. The expected secondary detector measurement as output from the best-fit line equation may then be compared to the actual secondary detector measurement to predict whether the detected particle should be sorted into the predicted fluorochrome population associated with the best-fit line equation. In one example, the detected particle may be sorted into the particular predicted fluorochrome population whose best-fit line equation results in the smallest difference between the expected detector measurement (equation output) and actual detector measurement. In another example, the detected particle may be sorted into a predicted fluorochrome population if the actual and expected detector measurements of the particle are within a threshold of each other (such as if the actual detector measurement is between a lower and/or upper threshold surrounding the expected detector measurement calculated with the best-fit line equation).

Figure 3D:
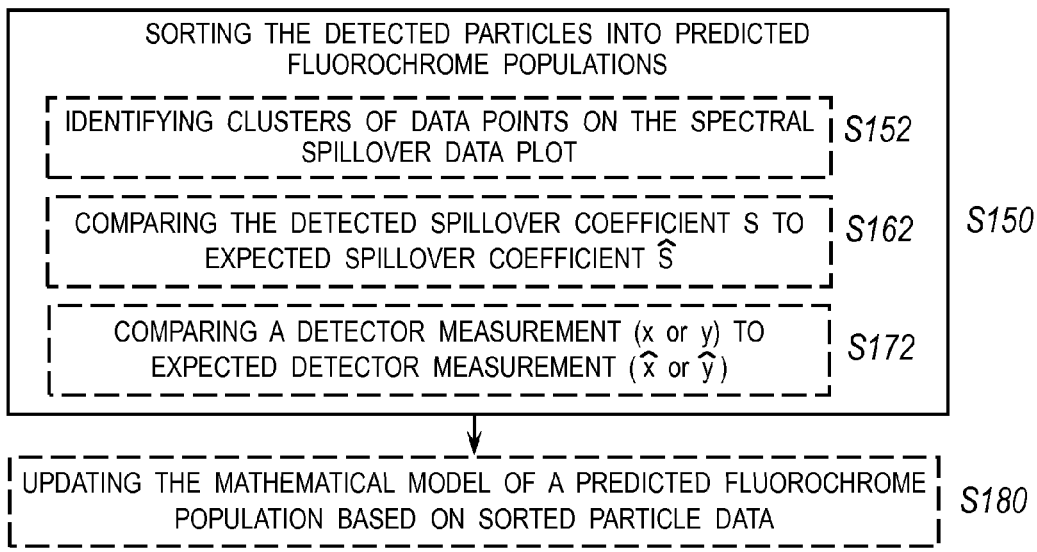

As shown in FIG. 3D, the method may further include updating the mathematical model of a predicted fluorochrome population S180 (e.g., the best-fit line of the fluorochrome population on a spectral spillover plot) based on the sorted particle data. For instance, each time the method is performed, the best-fit line may be recalculated with the incorporation of new data points after the detected particles are sorted into respective predicted fluorochrome populations based on a prior best-fit line (e.g., most up-to-date, or any other prior version). In this manner, the best-fit line characterizing each predicted fluorochrome population on the spectral spillover plots may be continually refined as more data points are obtained, thereby treating each spectral spillover data plot also as a spectral spillover calibration plot for future analyses. Furthermore, the method may further include storing the updated best-fit line.

In alternative embodiments, the step of sorting the detected particles S150 into predicted fluorochrome populations may include any combination of the above variations. In some cases, the detected spillover coefficient may not match any of the possible expected spillover coefficients (or, in the third variation of the sorting step, actual detector measurements may not match any of the possible expected detector measurements). In such cases, the particle may be tagged with two or more fluorochromes or with an unidentifiable fluorochrome. However, for a detection event in which the fluorochrome labeling is unknown, a comparison of actual channel numbers for any two modeled detectors and the expected channel numbers (based on a best-fit line equation, as in the third variation of the sorting step) can determine whether the detection event likely belongs to a single-stained or double-stained population (labeled with one or two fluorochromes, respectively).

Figure 4A:
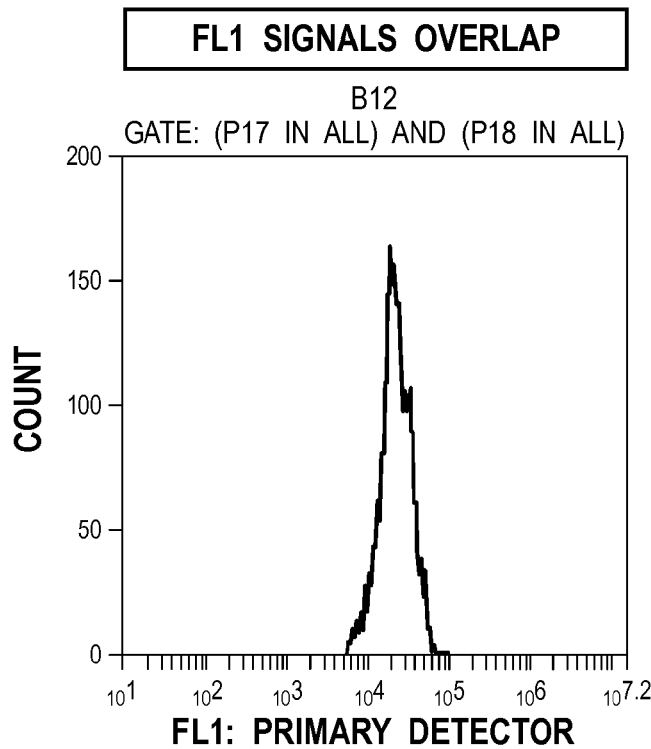
FIGS. 4A and 4B are examples of histograms of data plotted in the method of a preferred embodiment.
Figure 4B:
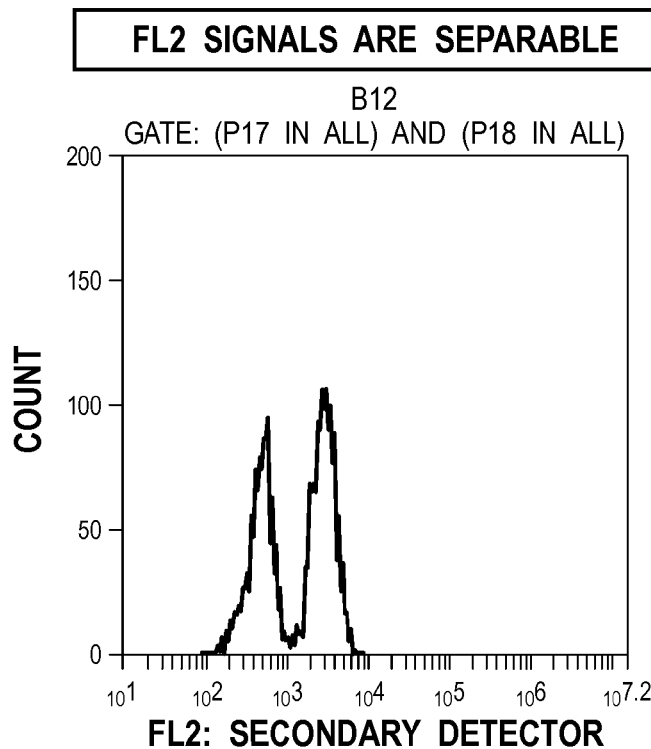

The method may additionally and/or alternatively include plotting the first and/or second data set on a histogram representative of the signal received by its primary detector, and/or the step of plotting the first and/or second data set on a histogram representative of the signal received by its secondary detector. In some cases, such as shown in FIG. 4A, the histogram may not enable sorting the detected particles into distinct predicted fluorochrome populations because of spectral overlap shown in the histogram. In some other cases, such as shown in FIG. 4B, the histogram may enable sorting the detected particles into distinct predicted fluorochrome populations. In both kinds of cases, the histogram may provide additional information relevant to analysis of the flow cytometry sample.

Figure 5:
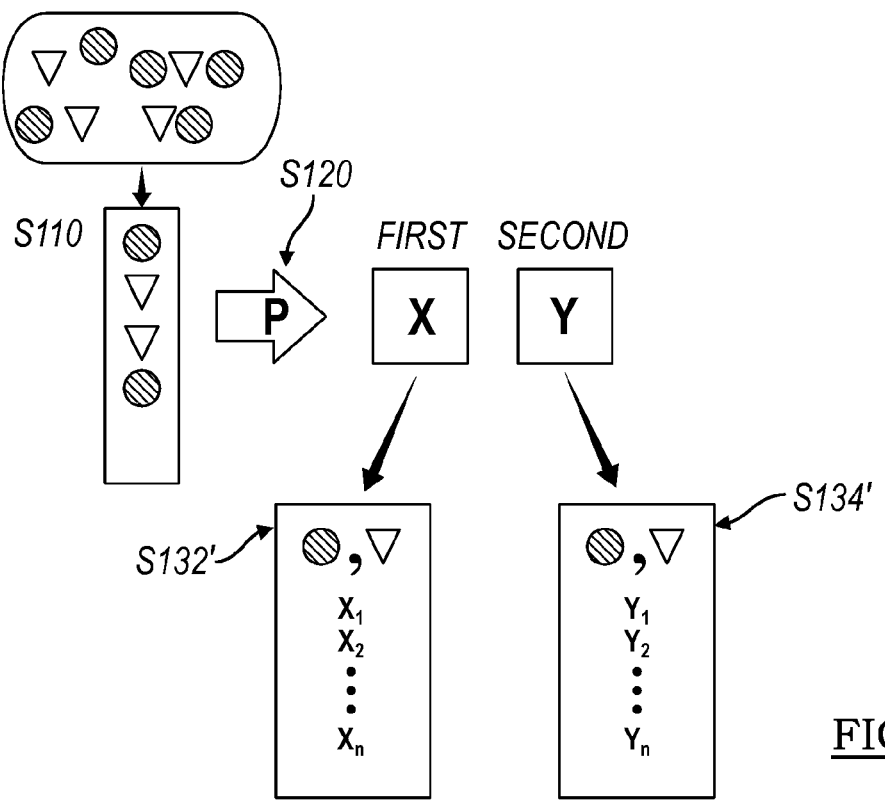
FIG. 5 is a schematic of the step of forming a data set in the method of another preferred embodiment.

In a second preferred embodiment of the method, the method 100 is similar to the first embodiment, except as described below. As shown in FIG. 5, in the method of the second preferred embodiment, the step of forming a data set includes forming a first data set based on the measurements of the first detector S132' and forming a second data set based on the measurements of the second detector S134'. In this embodiment, the first data set includes measurements (e.g., channel numbers) of light emitted by the first and second fluorochromes as detected by the first detector, and similarly the second data set includes detected measurements of light emitted by the first and second fluorochromes as detected by the second detector. In other words, in contrast to the first embodiment in which the first and second data sets correspond to the detections of first and second fluorochromes, in the second embodiment the first and second data sets correspond to the detections of the first and second detectors. However, in other embodiments the fluorochrome data may be organized in any suitable manner.

In the second preferred embodiment, the step of characterizing a detected spillover coefficient for each detected fluorochrome may be similar to that of the first preferred embodiment of the method, except the variation of calculating the detected spillover coefficient for a detected particle based on the first and second data sets S146 may include a slightly different calculation. For example, for an nth detected particle tagged with the first fluorochrome, dividing the channel number in the nth index of the second data set (corresponding to the secondary detector for the first fluorochrome) by the channel number in the nth index of the first data set (corresponding to the primary detector for the first fluorochrome). However, the detected spillover coefficient may be characterized in any suitable manner.

Figure 6:
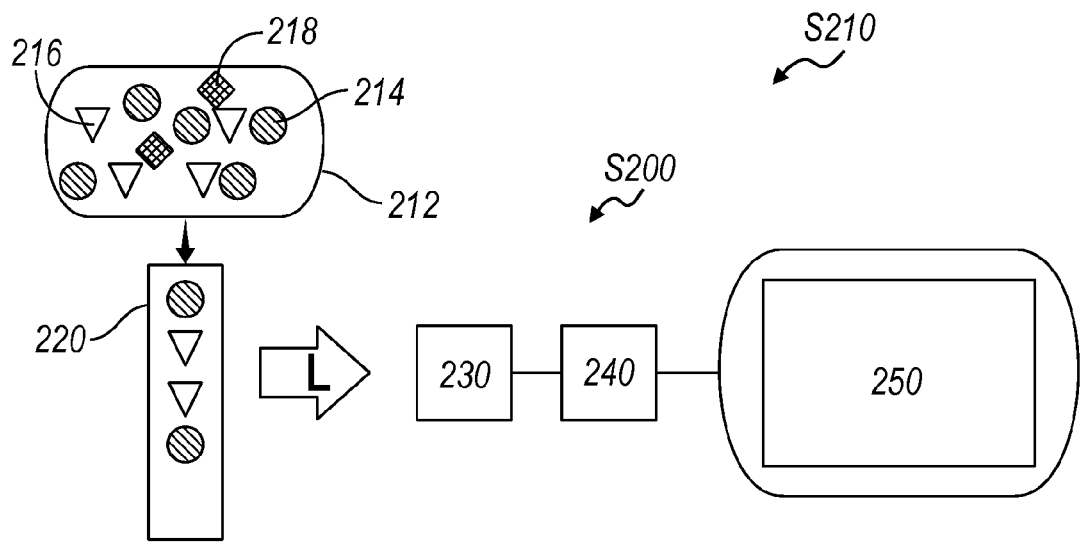
FIG. 6 is a schematic of the system of a preferred embodiment.

As shown in FIG. 6, the system 200 for detecting fluorochromes in a flow cytometer 210 of a preferred embodiment includes: an interrogation zone 220 that receives a sample 212 including particles tagged with at least one of a first fluorochrome 214 and a second fluorochrome 216, wherein the first and second fluorochromes have distinct spillover coefficients; a detection system 230 that detects particles passing through the flow cell, by detecting light L from energized first and second fluorochromes of the particles, and forms a data set based on detection of the first and second fluorochromes, respectively; and a processor 240 that generates a detected spillover coefficient for each detected particle from the data set and sorts the detected particles into predicted fluorochrome populations based on the detected spillover coefficient.

The interrogation zone 220 and detection system 240 are preferably designed to be integrated in a flow cytometer 210 capable of receiving a sample having particles tagged with fluorochromes. Particles preferably are manipulated to pass in substantially single file through the interrogation zone 220, where the fluorochromes are energized to emit light in respective spectra. The detection system 230 preferably includes a plurality of fluorescence detectors that detect light, including spectral spillover as described above. The fluorescence detectors preferably have a fixed gain (e.g., voltage and other amplification parameters) and a broad dynamic range, preferably of at least six decades. The detection system is preferably similar to that described in U.S. Pat. No. 7,739,060, but may alternatively be any suitable detection system.

The processor 240 performs data processing steps as described in the method of preferred embodiments for detecting fluorochromes in a flow cytometer. The processor may be any suitable computing device, such as a desktop or laptop computer adjacent to the flow cytometer (e.g., in a laboratory). In some embodiments, the processor may be in a handheld device, such as for portable data analysis (e.g., for portability within a hospital or clinic, or outside).

As shown in FIG. 6, the system may further include a display 250 that displays the data sets and/or spectral spillover data plots to a user. The display may include a user interface, such as for allowing a user to control operation of the flow cytometer system or to manipulate the data sets and/or plots (e.g., zooming or cropping data plots).

EXAMPLES

Figure 7:
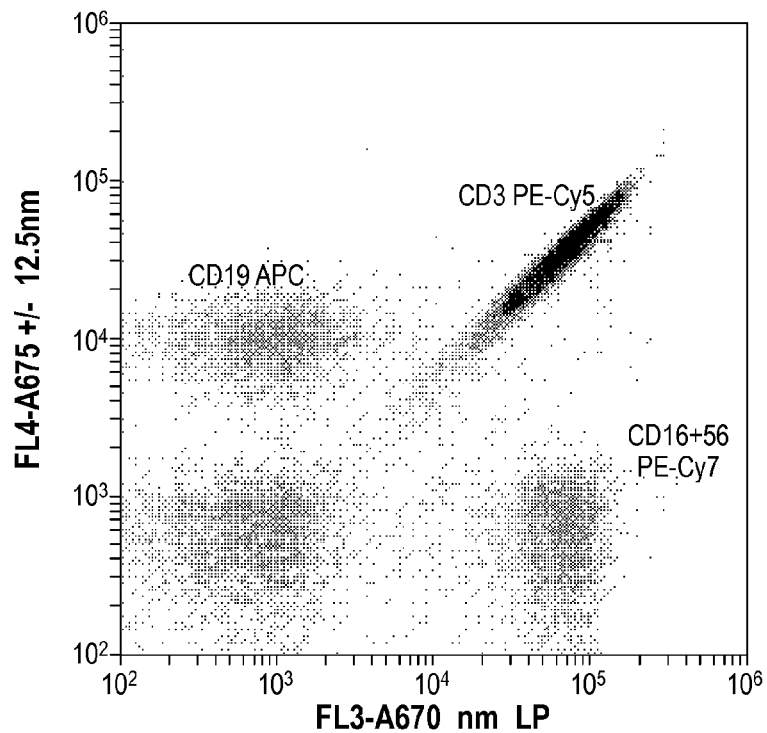
FIGS. 7-9 are example spectral spillover plots formed by the method of a preferred embodiment.

In a first example, as shown in FIG. 7, the method is performed on a human peripheral blood sample having three mutually exclusive cell populations tagged with CD19 APC, CD3 PE-Cy5, and CD16+56 PE-Cy7 fluorochromes. The method generates a plot in which the unique localization of these fluorochromes in the two-dimensional FL3 versus FL4 detection space allows the three cell populations to be analyzed using only two detectors.

Figure 8:
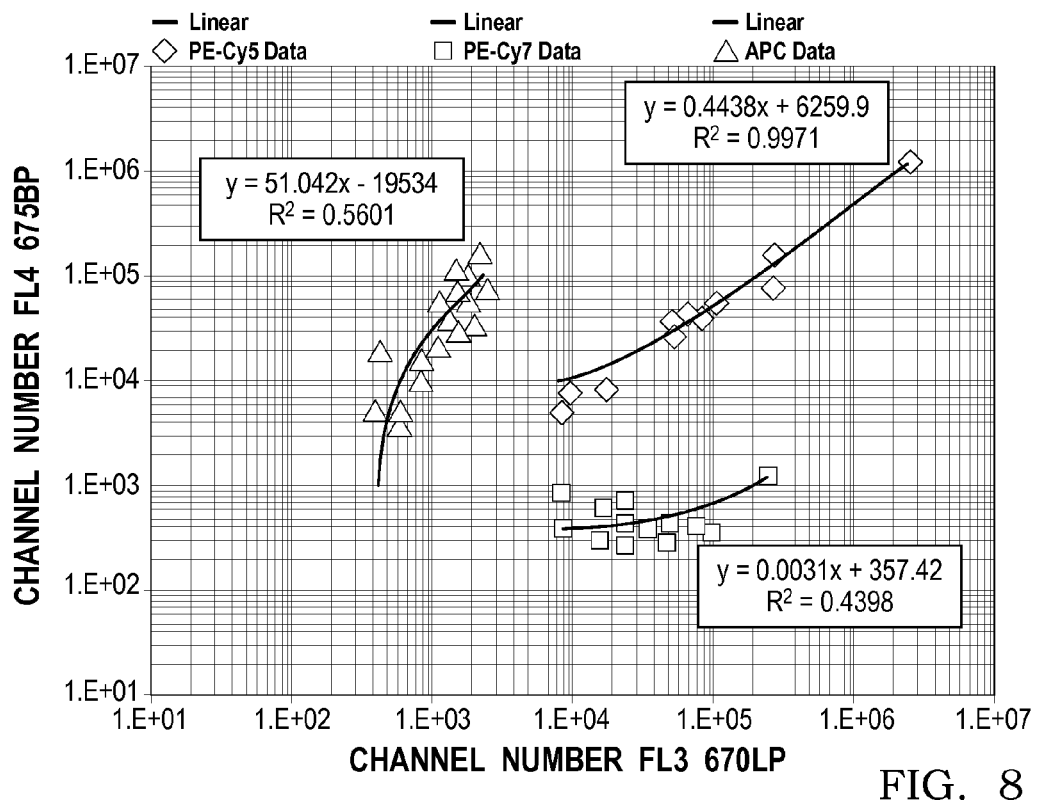

In a second example, the method is performed using ten different flow cytometers with substantially fixed gains, to mathematically model fluorescence spillover of fluorochromes. A sample including three groups of particles tagged with three fluorochromes (PE-Cy5, PE-Cy7, and APC) and a group of unstained particles are clustered in three distinct populations on a spectral spillover plot. As shown in FIG. 8, plotted points are the median FL3 and FL4 channel values for a variety of cell samples that are either unstained, APC-only stained (n=40, $r^2$=0.95), PE-Cy5-only stained (n=32, $r^2$=0.98), or PE-Cy7-only stained (n=27, $r^2$=0.19). A first fluorochrome population of particles tagged with PE-Cy5 is characterized by a best-fit line having a slope of 0.4438 that corresponds to the spillover coefficient for PE-Cy5 between detectors FL4 and FL3 (which are secondary and primary detectors for PE-Cy5, respectively). Similarly, a second fluorochrome population of particles tagged with PE-Cy7 is characterized by another best-fit line having a slope of 0.0031 corresponding to the spillover coefficient for PE-Cy7, and a third fluorochrome population of particles tagged with APC is characterized by a best-fit line having a slope of 51.042 (which in this example corresponds to the inverse spillover coefficient, as FL4 is the primary detector for APC and FL3 is the secondary detector for APC). The slopes for these three best-fit lines are distinct, which allows sorting of the detected particles among three distinct fluorochromes on the spectral spillover plot. Each of these three best-fit lines may be used to generate expected spillover coefficients or (inverse spillover coefficients) for future analysis of samples containing PE-Cy6, PE-Cy7, and/or APC.

Figure 9:
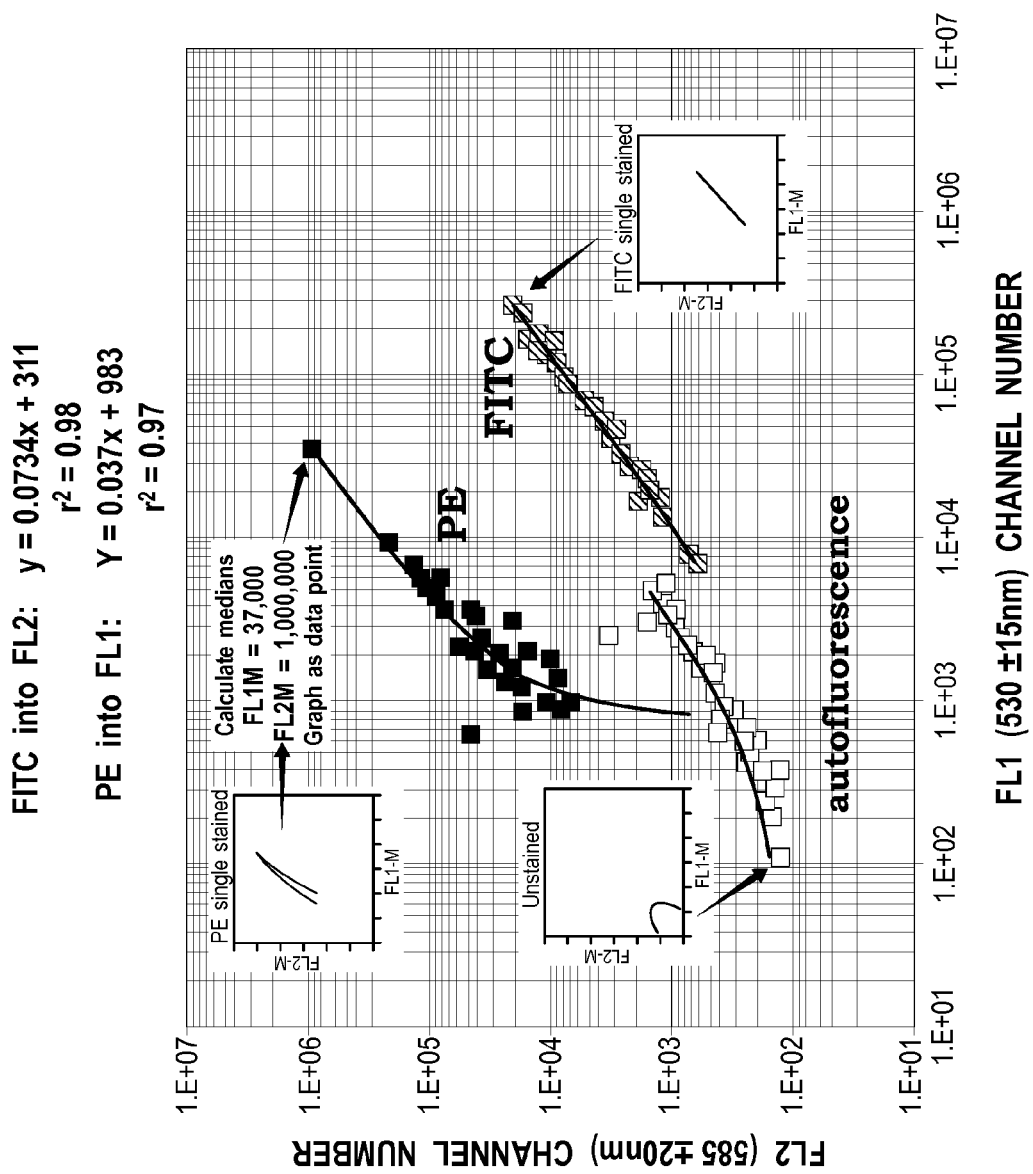

In a third example, the method is performed on 120 samples including unstained (autofluorescent), FITC-only stained, and PE-only stained samples, using 15 individual flow cytometers with substantially similar fixed gains and broad detection ranges. As shown in FIG. 9, compilation of the flow cytometric data shows the highly predictable detection of FITC and PE fluorescence across a range of intensities in FL1 and FL2 detectors. Plotted points are the median (M) FL1 and FL2 channel values for the various samples. The lines are the best-fit linear regression analysis of the data points, with $r^2$=0.98 for FITC-only stained data, and $r^2$=0.97 for PE-only stained data, and the best-fit lines characterize the distinct populations of FITC-only and PE-only stained particles. Flow cytometric plots (inset of FIG. 9) depict original data for several representative samples: unstained to 1.0 μm beads (lower left), PE-only stained and FITC-only stained human embryonal carcinoma cell line (upper left and lower right, respectively).

As a person skilled in the art will recognize from the previous detailed description and from the figures and claims, modifications and changes can be made to the preferred embodiments of the invention without departing from the scope of this invention defined in the following claims.

We claim:

1. A method for detecting fluorochromes in a flow cytometer, comprising:
   receiving a sample including particles each tagged with at least one of a first fluorochrome and a second fluorochrome, wherein the first and second fluorochromes have distinct spillover coefficients;
   detecting particles of the sample, including detecting the first and the second fluorochromes of the particles with a first detector and a second detector;
   forming a data set for detected particles based on the detection of the first and second fluorochromes of the particles;
   characterizing a detected spillover coefficient for each detected fluorochrome from the data set, wherein characterizing includes plotting measurements of the first detector on a first axis of a spectral spillover data plot representing at least a portion of the detected particles, and measurements of the second detector on a second axis of the spectral spillover data plot; and
   sorting the detected particles into predicted fluorochrome populations based on the detected spillover coefficients.

2. The method of claim 1, wherein detecting particles includes detecting fluorochromes with detectors having a fixed gain.

3. The method of claim 1, wherein detecting particles includes detecting fluorochromes with detectors having a broad dynamic range.

4. The method of claim 3, wherein detecting particles includes detecting fluorochromes with detectors having a range of at least six decades.

5. The method of claim 1, wherein detecting particles includes detecting particles tagged with the first fluorochrome primarily with the first detector and detecting particles tagged with the second fluorochrome primarily with the second detector.

6. The method of claim 1, wherein forming a data set includes forming a first data set based on the detection of the first fluorochrome and forming a second data set based on the detection of the second fluorochrome.

7. The method of claim 6, wherein forming a data set includes forming an array of channel numbers each corresponding to detected brightness of a fluorochrome signal.

8. The method of claim 7, wherein forming an array of channel numbers includes forming an array of pairs of channel numbers, wherein each pair includes a channel number for a primary detector and another channel number for a secondary detector.

9. The method of claim 1, wherein forming a data set includes forming a first data set based on the detections by the first detector and forming a second data set based on the detections by the second detector.

10. The method of claim 1, wherein plotting the first and second data sets includes plotting channel numbers of the first detector on the first axis and channel numbers of the second detector on the second axis.

11. The method of claim 1, wherein sorting the detected particles into predicted fluorochrome populations includes identifying a cluster of data points on the spectral spillover data plot corresponding to the first fluorochrome.

12. The method of claim 1, further comprising displaying the spectral spillover data plot to a user.

13. The method of claim 1, wherein characterizing a detected spillover coefficient includes calculating the detected spillover coefficient from the data set for each of at least a portion of the detected particles.

14. The method of claim 13, wherein calculating the detected spillover coefficient includes dividing data set elements corresponding to detection of a particle by a secondary detector by data set elements corresponding to detection of the particle by a primary detector.

15. The method of claim 14, wherein sorting the detected particles includes comparing the detected spillover coefficient to an expected spillover coefficient estimated with a best-fit line corresponding to the first or second fluorochrome on a spectral spillover calibration plot.

16. The method of claim 15, wherein comparing the detected spillover coefficient to an expected spillover coefficient includes comparing the detected spillover coefficient to the slope of the best-fit line.

17. The method of claim 1, wherein sorting the detected particles into predicted fluorochrome populations includes comparing the detected spillover coefficient to an expected spillover coefficient of at least one of the first and second fluorochromes.

18. The method of claim 1, wherein sorting the detected particles includes sorting each of at least a portion of the detected particles into a first predicted fluorochrome population corresponding to the first fluorochrome or into a second predicted fluorochrome population corresponding to the second fluorochrome.

19. The method of claim 1, wherein detecting particles further includes detecting a third fluorochrome of the particles having a third spillover coefficient and sorting the detected particles further includes sorting each of at least a portion of the detected particles into a third predicted fluorochrome population corresponding to the third fluorochrome.

20. The method of claim 19, wherein detecting the third fluorochrome includes detecting the third fluorochrome with the first and second detectors.

21. A system for detecting fluorochromes in a flow cytometer, comprising:
   an interrogation zone that receives a sample including particles tagged with at least one of a first fluorochrome and a second fluorochrome, wherein the first and second fluorochromes have distinct spillover coefficients;
   a detection system that detects particles passing through the flow cell, by detecting the first and second fluorochromes of the particles with a first detector and a second detector, and forms a data set based on detection of the first and second fluorochromes, respectively; and
   a processor that generates a detected spillover coefficient for each detected particle from the data set and sorts the detected particles into predicted fluorochrome populations based on the detected spillover coefficient, wherein the processor plots the data set on a spectral spillover data plot such that detections of the first detector are on a first axis of the plot and detections of the second detector are on a second axis of the spectral spillover data plot.

22. The system of claim 21, wherein the detection system has a fixed gain.

23. The system of claim 21, wherein the detection system has a broad dynamic range.

24. The system of claim 23, wherein the detection system has a range of at least six decades.

25. The system of claim 21, further comprising a display that presents the spectral spillover data plot to a user.

26. The system of claim 21, wherein the processor sorts a detected particle into a particular fluorochrome population by comparing the detected spillover coefficient for the detected particle to an expected spillover coefficient.

27. The system of claim 26, wherein the processor calculates the expected spillover coefficient using a known best-fit line corresponding to the particular fluorochrome population on a spectral spillover data plot.

* * * * *